(12) United States Patent
Chareyre et al.

(10) Patent No.: US 11,406,932 B2
(45) Date of Patent: Aug. 9, 2022

(54) MEMBRANE PERMEATION TREATMENT WITH ADJUSTMENT OF THE NUMBER OF MEMBRANES USED AS A FUNCTION OF THE PRESSURE OF THE FEED GAS FLOW

(71) Applicant: L'Air Liquide, Societe Anonyme pour l'Etude et l'Exploitation des Procedes Georges Claude, Paris (FR)

(72) Inventors: Jean-Marc Chareyre, Voiron (FR); Veronique Grabie, Coublevie (FR); Golo Zick, Fontaine (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 17/336,131

(22) Filed: Jun. 1, 2021

(65) Prior Publication Data

US 2021/0283549 A1 Sep. 16, 2021

Related U.S. Application Data

(62) Division of application No. 16/536,307, filed on Aug. 8, 2019, now Pat. No. 11,052,345.

(30) Foreign Application Priority Data

Aug. 8, 2018 (FR) .................................. FR 1857384

(51) Int. Cl.
*B01D 53/22* (2006.01)
*C07C 7/00* (2006.01)
*C07C 7/144* (2006.01)

(52) U.S. Cl.
CPC ............ *B01D 53/226* (2013.01); *C07C 7/005* (2013.01); *C07C 7/144* (2013.01); *B01D 2053/221* (2013.01)

(58) Field of Classification Search
CPC .. B01D 53/225; B01D 53/226; B01D 53/228; B01D 53/30; B01D 2053/221;
(Continued)

(56) References Cited

U.S. PATENT DOCUMENTS

| 8,999,038 B2 | 4/2015 | Ungerank et al. |
| 2007/0125537 A1 | 6/2007 | Lockhandwala et al. |

(Continued)

FOREIGN PATENT DOCUMENTS

| EP | 2 735 355 | 5/2014 |
| FR | 3 010 640 | 3/2015 |

OTHER PUBLICATIONS

French Search Report and Written Opinion for FR 1 857 384, dated May 29, 2019.

*Primary Examiner* — Youngsul Jeong
*Assistant Examiner* — Jason Y Chong
(74) *Attorney, Agent, or Firm* — Christopher J. Cronin

(57) ABSTRACT

A facility and method for membrane permeation treatment of a feed gas flow containing at least methane and carbon dioxide that includes a compressor, a pressure measurement device, at least one valve, and first, second, third, and fourth membrane separation units for separation of $CO_2$ from $CH_4$ to permeates enriched in $CO_2$ and retentates enriched in $CH_4$, respectively. The at least one valve adjusts the number of membranes combined and connected to the flow of gas entering into at least one of the membrane separation units as a function of the pressure recorded by the pressure measurement device.

8 Claims, 3 Drawing Sheets

(58) Field of Classification Search
CPC ........ B01D 2256/245; B01D 2257/504; B01D 2258/05; C10L 2290/06; C10L 2290/12; C10L 2290/26; C10L 2290/46; C10L 2290/548; C10L 2290/58; C10L 2290/60; C10L 3/104; Y02C 20/40; C07C 7/005; C07C 7/144

See application file for complete search history.

(56) References Cited

U.S. PATENT DOCUMENTS

| | | |
|---|---|---|
| 2012/0000355 A1 | 1/2012 | Sharma et al. |
| 2015/0336046 A1 | 11/2015 | Ungerank et al. |
| 2016/0229771 A1 | 8/2016 | Paget et al. |

US 11,406,932 B2

MEMBRANE PERMEATION TREATMENT WITH ADJUSTMENT OF THE NUMBER OF MEMBRANES USED AS A FUNCTION OF THE PRESSURE OF THE FEED GAS FLOW

CROSS-REFERENCE TO RELATED APPLICATIONS

The present application is a divisional of U.S. application Ser. No. 16/536,307 filed Aug. 8, 2019, which claims the benefit of priority under 35 U.S.C. § 119 (a) and (b) to French patent application No. FR1857384, filed Aug. 8, 2018, the entire contents of which are incorporated herein by reference.

BACKGROUND

Field of the Invention

The present invention relates to a facility for the treatment by membrane permeation of a gas stream containing at least methane and carbon dioxide in order to produce a methane-rich gas stream, of which the methane content meets the requirements of its use, and to a method for controlling such a facility.

It relates in particular to the purification of biogas, with the aim of producing biomethane in accordance with the specifications for injection into a natural gas network.

Related Art

Biogas is the gas produced as organic matter breaks down in the absence of oxygen (anaerobic fermentation), also referred to as methanization. This may be natural breakdown—it is thus found in marshland or in household waste landfill—but the production of biogas may also result from the methanization of waste in a dedicated reactor referred to as a methanizer or digester.

Because of its chief constituents—methane and carbon dioxide—biogas is a powerful greenhouse gas; at the same time, it also constitutes a source of renewable energy that is appreciable in the context of the increasing scarcity of fossil fuels.

Biogas contains mainly methane ($CH_4$) and carbon dioxide ($CO_2$) in proportions that can vary according to the way in which it is obtained, but also contains, in smaller proportions, water, nitrogen, hydrogen sulfide, oxygen and other organic compounds, in trace form.

Depending on the organic matter that has been broken down and on the techniques used, the proportions of the components differ, although on average biogas contains, on a dry gas basis, from 30 to 75% methane, from 15 to 60% $CO_2$, from 0 to 15% nitrogen, from 0 to 5% oxygen and trace compounds.

Biogas is put to profitable use in various ways. It may, after light treatment, be put to profitable use near the production site in order to supply heat, electricity or a mixture of both (cogeneration); the high carbon dioxide content reduces its calorific value, increases the cost of compression and transport and limits the economic benefit of this way putting it to profitable use nearby.

Purifying the biogas to a greater degree allows it to be put to broader use, in particular, extensive purification of the biogas yields a biogas that has been purified to the specifications of natural gas and which can be substituted for the latter; biogas thus purified is known as "biomethane". Biomethane thus supplements the natural gas resources with a renewable proportion produced within the territories; it can be put to exactly the same uses as natural gas of fossil origin. It can be fed into a natural gas network, a vehicle filling station; it can also be liquefied to be stored in the form of liquefied natural gas (LNG) etc.

The ways in which the biomethane is put to profitable use are determined according to the local context: local energy requirements, possibilities for putting it to profitable use as a biomethane fuel, and whether there is a natural gas transport or distribution network nearby, in particular. By creating synergy between the various parties operating in a given territory (farmers, manufacturers, civic authorities), the production of biomethane assists the territories in acquiring greater self-sufficiency in terms of energy.

There are a number of steps that need to be completed between collecting the biogas and obtaining the biomethane, the end-product that can be compressed or liquefied.

In particular, there are several steps needed prior to the treatment which is aimed at separating the carbon dioxide in order to produce a stream of purified methane. A first step is to compress the biogas which has been produced and brought in at atmospheric pressure, and this compression can be obtained—in the conventional way—using a lubricated screw compressor. The next steps are aimed at ridding the biogas of its corrosive components which are hydrogen sulfide and the volatile organic compounds (VOCs), the technologies used are, in the conventional way, pressure swing adsorption (PSA) and capture on activated carbon. Next comes the step which consists in separating the carbon dioxide in order ultimately to obtain methane at the purity required for its subsequent use.

Carbon dioxide is a contaminant typically present in natural gas and it is common practice to need to remove it therefrom. Varying technologies are used for this depending on the situation; among these, membrane technology performs particularly well when the $CO_2$ content is high; and it is therefore particularly effective for separating the $CO_2$ present in biogas and in particular in landfill gas.

Membrane gas separation methods used for purifying a gas, whether they employ one or more membrane stages, need to make it possible to produce a gas at the required quality, at a low cost, while at the same time minimizing the losses of the gas that is to be put to profitable use. Thus, in the case of biogas purification, the separation performed is chiefly a $CH_4/CO_2$ separation which needs to allow the production of a gas containing, depending on its use, more than 85% $CH_4$, preferably more than 95% $CO_2$, more preferentially more than 97.5% $CH_4$, while minimizing the $CH_4$ losses in the residual gas and the cost of purification, the latter to a large extent being associated with the electricity consumption of the device that compresses the gas upstream of the membranes.

It is preferable for the facilities that allow the production of a methane-enriched gas flow to be able to control the methane loss.

On that basis, one problem that arises is that of providing a facility that makes it possible to obtain a stream of methane at a constant concentration.

SUMMARY OF THE INVENTION

One solution of the present invention is a facility for the membrane permeation treatment of a feed gas flow containing at least methane and carbon dioxide, comprising:

a compressor for compressing the feed gas flow, a first membrane separation unit able to receive the gas flow corning from the compressor and to supply a first permeate and a first retentate, a second membrane separation unit able to receive the first retentate and to supply a second permeate and a second retentate, a third membrane separation unit able to receive the first permeate and to supply a third permeate and a third retentate, a fourth membrane separation unit able to receive the third retentate and to supply a fourth permeate and a fourth retentate, at least a first means for measuring the pressure of the feed gas flow at the inlet of the first membrane separation unit, and at least one means for adjusting the number of membranes combined and connected to the entering gas flow in at least one of the membrane separation units as a function of the measurement recorded by the first measuring means.

DETAILED DESCRIPTION OF THE INVENTION

Figure 2:
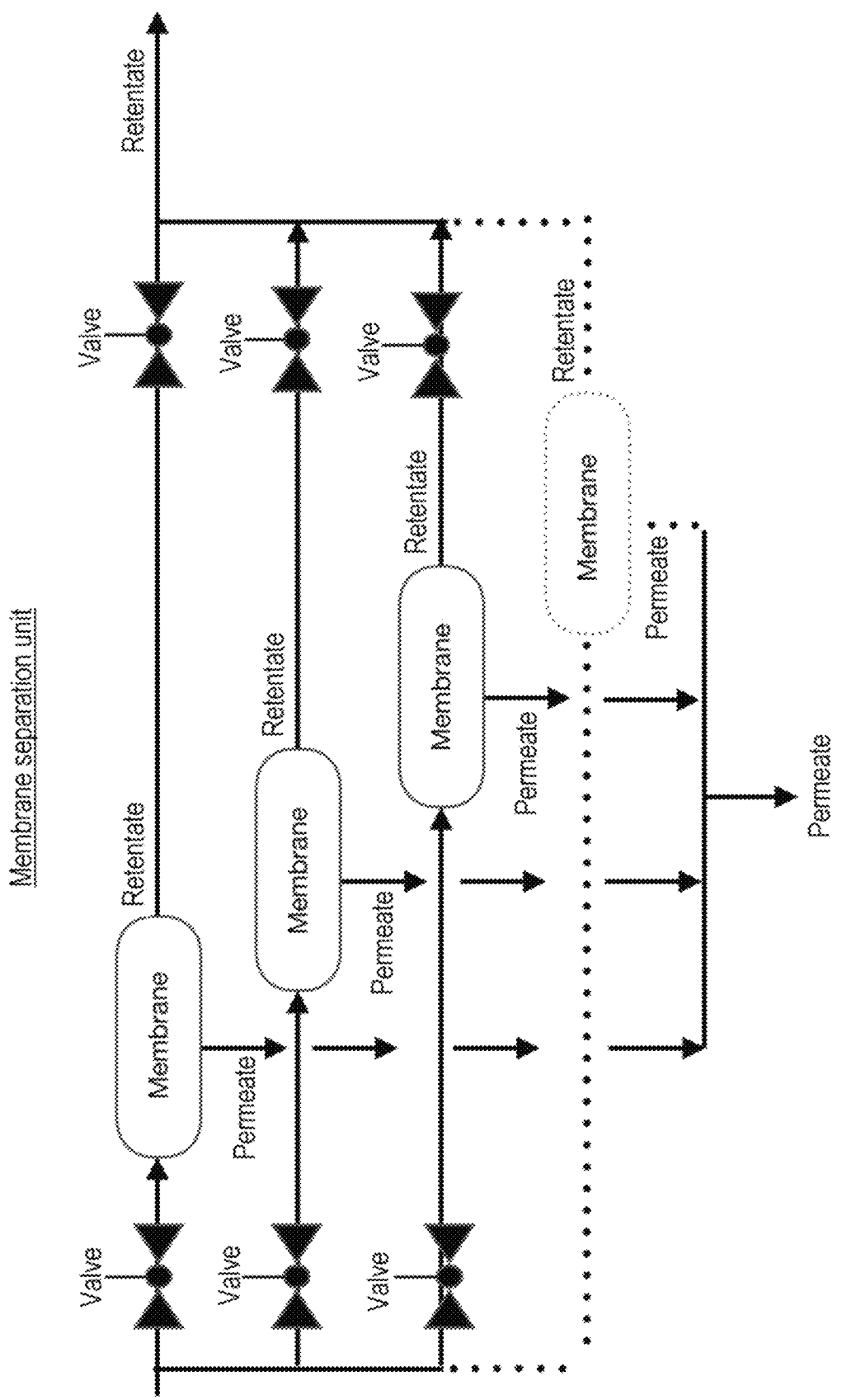
FIG. 2 is a schematic of a membrane separation unit incorporating the inventive technique.

Preferably, the membranes combined in one and the same membrane separation unit are placed in parallel as illustrated in FIG. 2. FIG. 2 clearly shows that, by means of the valves, the flow entering said membrane separation unit does or does not pass through the membranes.

Figure 1:
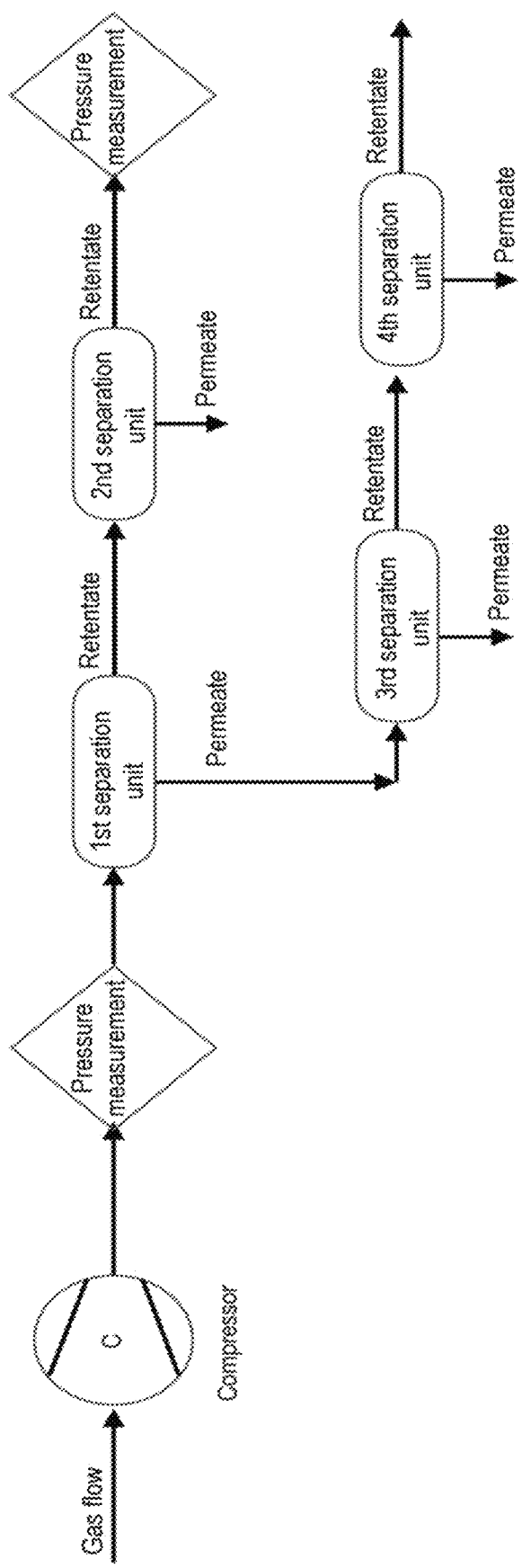
FIG. 1 is a schematic of an example of a facility incorporating the inventive technique.

An example of a facility according to the invention is depicted in FIG. 1. Depending on the case, the facility according to the invention may have one or more of the following features:

the pressure measurement device measures the pressure of the gas flow at the inlet of the first separation unit or the pressure of the second retentate of the second separation unit;

the means for adjusting the number of membranes comprises at least one valve. Preferably, said valve will be included in the membrane separation unit in which it is desired to adjust the number of membranes;

the fourth retentate is recycled to the compressor for compressing the feed gas flow;

the membranes used in the membrane separation units have the same selectivity;

at least one membrane separation unit comprises at least two membranes with the same selectivity;

at least one membrane separation unit comprises at least two membranes with different selectivities;

at least one membrane separation unit uses a membrane with a selectivity different from the selectivity of the membranes of the other membrane separation units.

A subject of the present invention is also a method for controlling a facility according to the invention, comprising the following steps:

measuring a pressure of the feed gas flow at the inlet of the first membrane separation unit, comparing this measurement with a setpoint value, and of determining the difference with respect to this setpoint value, and adjusting the number of membranes combined and connected to the entering gas flow, in at least one of the membrane separation units as a function of the difference determined, so as to keep the methane concentration in the second retentate constant.

Depending on the case, the method according to the invention can exhibit one or more of the features below:

the step of adjusting the number of membranes comprises: successively adding a membrane in the first membrane separation unit, then in the third membrane separation unit and, finally, in the second membrane separation unit, or successively withdrawing a membrane in the first membrane separation unit, then in the third membrane separation unit and, finally, in the second membrane separation unit;

the measuring step, the comparing step and the adjusting step are carried out automatically by data transmission and data processing device.

According to a second alternative, the method for controlling a facility according to the invention comprises the following steps:

a step (i) of measuring the pressure of the feed gas flow at the inlet of the first membrane separation unit, a step (ii) of adjusting the number of membranes combined and connected to the entering gas flow in at least one of the membrane separation units according to the following rule:

When the pressure measured in step (i) goes above a previously fixed threshold S1, a membrane is added in the first membrane separation unit, then in the third membrane separation unit and, finally, in the second membrane separation unit;

When the pressure measured in step (i) goes below a previously fixed threshold S2, a membrane is withdrawn in the first membrane separation unit, then in the third membrane separation unit and, finally, in the second membrane separation unit.

Depending on the case, the process according to this second alternative can exhibit one or more of the following characteristics:

the measuring step and the adjusting step are carried out automatically by data transmission and data processing means. A data transmission and data processing means may for example be an industrial processor of the programmable controller type;

the feed gas flow is biogas.

Figure 3:
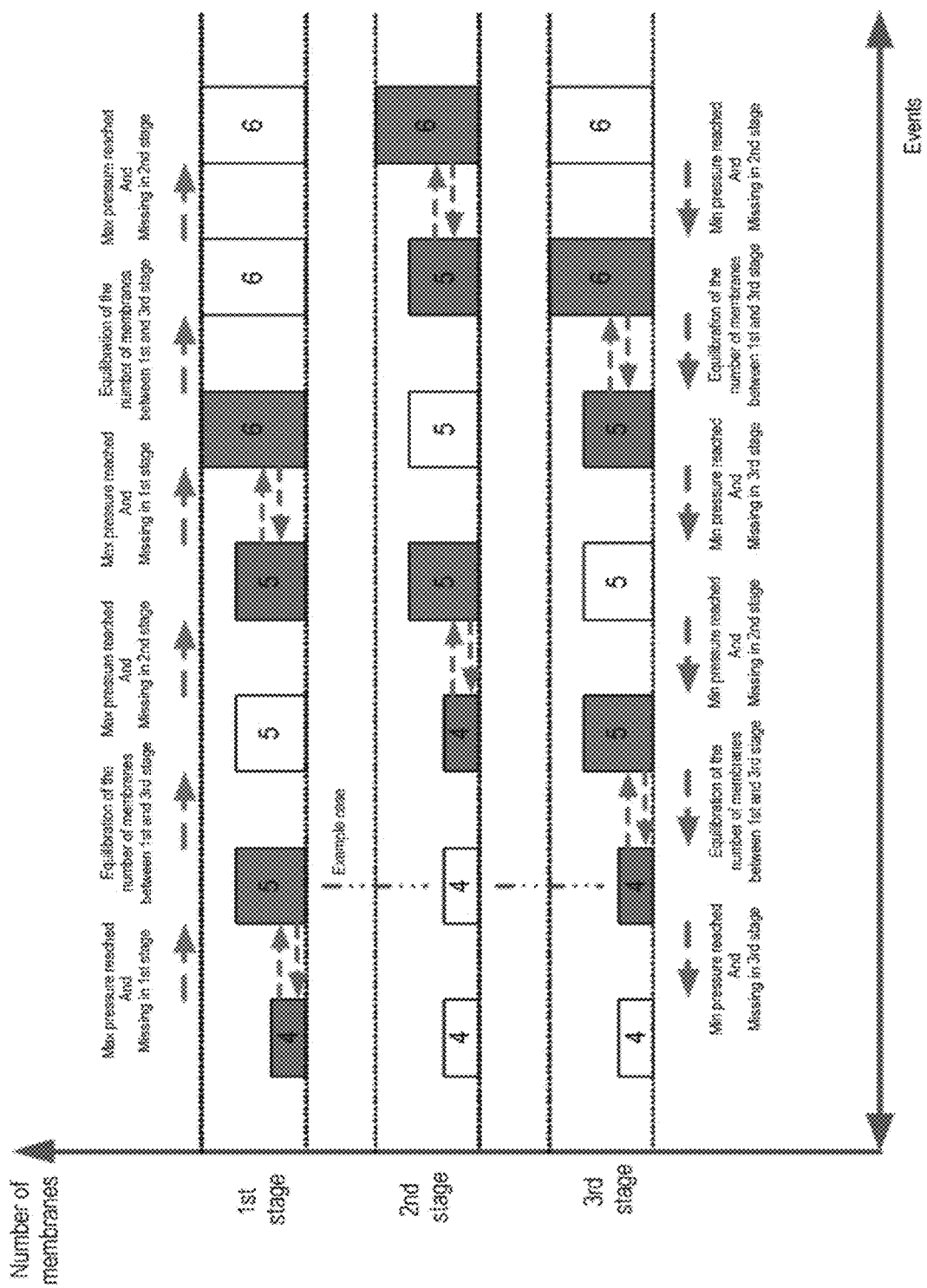
FIG. 3 is a graph indicating the number of membranes per separation unit as a function of events.

The present invention will be described in greater detail by means of FIG. 3. FIG. 3 is a graphic indicating the number of membranes per separation unit as a function of the events. In the graphic, the first membrane separation unit is referred to as the first stage, the second membrane separation unit is referred to as the second stage and the third membrane separation unit is referred to as the third stage.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A facility for the membrane permeation treatment of a feed gas flow containing at least methane and carbon dioxide, comprising:
   a compressor for compressing the feed gas flow;
   a first membrane separation unit able to receive a flow of gas from the compressor and supply a first permeate and a first retentate, the first membrane separation unit comprising a plurality of membranes;
   a second membrane separation unit able to receive the first retentate and supply a second permeate and a second retentate, the second membrane separation unit comprising a plurality of membranes;
   a third membrane separation unit able to receive the first permeate and supply a third permeate and a third retentate, the third membrane separation unit comprising a plurality of membranes;
   a fourth membrane separation unit able to receive the third retentate and supply a fourth permeate and a fourth retentate, the fourth membrane separation unit comprising a plurality of membranes;
   a pressure measurement device able to measure a pressure of a flow of gas flowing into the first membrane separation unit or of the second retentate; and
   at least one valve able to adjust a number of the membranes in at least one of the membrane separation units that receive a flow of gas therein as a function of the measured pressure.

2. The facility of claim 1, wherein the pressure measurement device measures a pressure of gas flow at an inlet of the first separation unit.

3. The facility of claim 1, wherein the pressure measurement device measures a pressure of the second retentate.

4. The facility of claim 1, wherein the fourth retentate is recycled to the compressor.

5. The facility of claim 1, wherein the membranes of each one of the membrane separation units has a same selectivity.

6. The facility of claim 1, wherein at least one of the plurality of membranes of at least one membrane separation unit has a selectivity different from that of other of the plurality of membranes of said at least one membrane separation unit.

7. The facility of claim 1, wherein at least one of the membrane separation units comprises at least two membranes with the same selectivity.

8. The facility of claim 1, wherein at least one of the membrane separation units comprises at least two membranes with different selectivities.

* * * * *